(12) United States Patent
Lee et al.

(10) Patent No.: US 7,385,095 B2
(45) Date of Patent: Jun. 10, 2008

(54) INDENE DERIVATIVES AND ORGANIC LIGHT EMITTING DIODE USING THE SAME

(75) Inventors: Dae Woong Lee, Daejeon Metropolitan (KR); Jae Soon Bae, Daejeon Metropolitan (KR); Dong Hoon Lee, Seoul (KR); Kong Kyeom Kim, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/583,026

(22) Filed: Oct. 19, 2006

(65) Prior Publication Data
US 2007/0090353 A1 Apr. 26, 2007

(30) Foreign Application Priority Data
Oct. 21, 2005 (KR) ............ 10-2005-0099872

(51) Int. Cl.
*C07C 13/54* (2006.01)
*C07C 13/62* (2006.01)
*C07C 2/02* (2006.01)
*C07C 211/54* (2006.01)
*C07D 213/22* (2006.01)
*C07D 277/62* (2006.01)
*C07F 7/08* (2006.01)

(52) U.S. Cl. ............ 585/26; 585/425; 585/427; 546/257; 546/258; 546/259; 548/160; 556/489; 564/426; 564/427

(58) Field of Classification Search ............ None
See application file for complete search history.

(56) References Cited

U.S. PATENT DOCUMENTS 5,935,721 A 8/1999 Shi et al.

FOREIGN PATENT DOCUMENTS

| JP | 2001-288377 | 10/2001 |
|---|---|---|
| JP | 2003-313156 | 11/2003 |
| JP | 2004-059535 | 2/2004 |
| JP | 2005-008600 | 1/2005 |
| WO | WO 03-012890 A2 | 2/2003 |

*Primary Examiner*—Brian J. Davis
(74) *Attorney, Agent, or Firm*—McKenna Long & Aldridge LLP

(57) ABSTRACT

The present invention provides an indene derivatives having a new structure and an organic light-emitting diode using the same. The organic light-emitting diode according to the present invention shows improved effects in efficiency, driving voltage and stability.

6 Claims, No Drawings

INDENE DERIVATIVES AND ORGANIC LIGHT EMITTING DIODE USING THE SAME

TECHNICAL FIELD

The present invention relates to an indene derivative having a new structure and an organic light-emitting diode using the same.

This application claims priority benefits from Korean Patent Application No. 10-2005-0099872, filed on Oct. 21, 2005, the entire contents of which are fully incorporated herein by reference.

BACKGROUND ART

In general, the term "organic light-emitting phenomenon" refers to a phenomenon in which electric energy is converted to light energy by means of an organic material. The organic light-emitting diode using the organic light-emitting phenomenon has a structure usually comprising an anode, a cathode and an organic material layer interposed therebetween. Herein, the organic material layer may be mostly formed in a multilayer structure comprising layers of different materials, for example, the hole-injecting layer, the hole-transporting layer, the light-emitting layer, the electron-transporting layer, the electron-injecting layer and the like, in order to improve efficiency and stability of the organic light-emitting diode. In the organic light-emitting diode having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such an organic light-emitting diode is known to have characteristics such as self-luminescence, high brightness, high efficiency, low drive voltage, wide viewing angle, high contrast and high-speed response.

The materials used for the organic material layer of the organic light-emitting diode can be classified into a light-emitting material and a charge-transporting material, for example, a hole-injecting material, a hole-transporting material, an electron-transporting material and an electron-injecting material, according to their functions. The light-emitting material can be classified into a high molecular weight-type and a low molecular weight-type, according to their molecular weight, or fluorescent materials, emitting light from singlet excited state of electrons, and phosphorescent materials, emitting light from, triplet excited state of electrons, according to their emitting mechanism. Further, the light-emitting material can be divided into a blue, green or red light-emitting material and a yellow or orange light-emitting material required for giving more natural color, according to a light-emitting color.

On the other hand, an efficiency of a device is lowered owing to maximum luminescence wavelength moved to a longer wavelength due to the interaction between molecules, deterioration of color purity and reduction in light-emitting efficiency when only one material is used for the light-emitting material, and therefore a host/dopant system can be used as the light-emitting material for the purpose of enhancing color purity and light-emitting efficiency through energy transfer. When dopants, having smaller energy band gap than that of hosts, are mixed into light-emitting layer in a small amount, excitons generated from the light-emitting layer are transported to the dopants and then emit light efficiently. In this case, since a wavelength of emitted light shifts from a wavelength of the hosts to a wavelength of the dopants, light having a desired wavelength can be obtained depending on the type of the dopant.

In order to allow the organic light-emitting diode to fully exhibit the above-mentioned excellent characteristics, a material constituting the organic material layer in the device, for example, a hole-injecting material, a hole-transporting material, a light-emitting material, an electron-transporting material and an electron-injecting material should be essentially composed of a stable and efficient material. However, the development of a stable and efficient organic material layer material for the organic light-emitting diode has not yet been fully realized. Accordingly, the development of new materials is continuously desired.

DISCLOSURE

Technical Problem

The present inventors have found an indene derivative having a new structure and found that an organic light-emitting diode shows effects including an improved efficiency, a reduced driving voltage, and an improved stability, when an organic material layer of the organic light-emitting diode is formed with the indene derivative.

Accordingly, it is an object of the present invention to provide an indene derivative and an organic light-emitting diode using the same.

Technical Solution

The present invention provides a compound represented by the following formula (1):

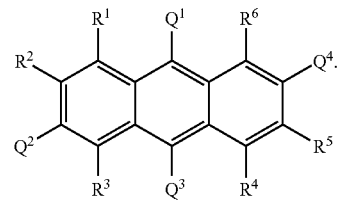

Formula 1 wherein at least one of $Q^1$ to $Q^4$ are a group represented by the following formula (2), the reminders of $Q^1$ to $Q^4$ that are not represented by the following formula (2) and $R^1$ to $R^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted cycloalkyl group, a substituted or unsubstituted cycloalkenyl group, a substituted or unsubstituted aryl group, a substituted or unsubstituted arylamine group, a substituted or unsubstituted heterocyclic group, a substituted or unsubstituted silane group, a substituted or unsubstituted boric group, a substituted or unsubstituted amino group, a nitrile group, a nitro group, a halogen group, a substituted or unsubstituted amide group, and a substituted or unsubstituted ester group, and they may be bonded with an adjacent group to form an aliphatic, aromatic or hetero fused ring, Formula 2

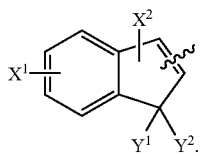

wherein $X^1$, $X^2$, $Y^1$ and $Y^2$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^1$ and $Y^2$ may be bonded with each other to form a cycloalkyl group or an aryl group.

Further, the invention provides an organic light-emitting diode comprising a first electrode, a second electrode and an organic Material layer arranged between the first electrode and the second electrode, in which the organic material layer comprises the compound represented by the above formula (1).

Advantageous Effects

A compound according to the present invention is an indene derivatives having a new structure. The compound can be used as materials for organic layers of organic light-emitting diodes owing to its structural characteristics.

Best Mode

Hereinafter, the compound of the invention will be explained in detail.

The alkyl group, alkoxy group and alkenyl group of substituents in the above formula (1) and (2) preferably have 1 to 30 carbon atoms.

Examples of the aryl group of substituents in the above formula (1) and (2) include, but are not limited to, a phenyl group, a naphthyl group, an anthracenyl group, a biphenyl group, a pyrenyl group, a perylenyl group, etc.

Examples of the arylamine group of substituents in the above formula (1) and (2) include, but are not limited to, a diphenylamine group, a phenylnaphthylamine group, a ditolylamine group, a phenyltolylamine group, a carbazolyl group and a triphenylamine group.

Examples of the heterocyclic group of substituents in the above formula (1) and (2) include, but are not limited to, a pyridyl group, an acridinyl group, a thienyl group, an imidazolyl group, an oxazolyl group, a thiazolyl group, a quinolyl group, etc.

Examples of the halogen group of substituents in the above formula (1) include fluorine, chlorine, bromine and iodine.

Examples of substituent that may be bonded to the substituents of the above formula (1) and (2) include a halogen group, a hydroxy group, a substituted or unsubstituted straight or branched alkyl group, a substituted or unsubstituted aryl group, a substituted or unsubstituted heteroaryl group, a substituted or unsubstituted amine group, a substituted or unsubstituted cycloalkyl group, a substituted or unsubstituted arylamine group, a substituted or unsubstituted straight or branched alkenyl group, a nitro group, a nitrile group, a substituted or unsubstituted silane group, etc.

Examples of the compound of the formula 1 include the following compound represented by formula 1-1.

Formula 1-1

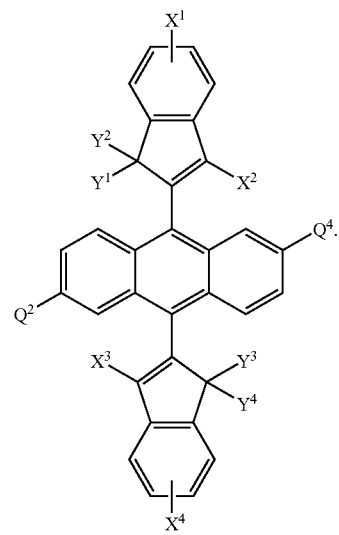

wherein $Q^2$, $Q^4$, $X^1$, $X^2$, $Y^1$ and $Y^2$ are as defined in Formula (1), $X^3$, $X^4$, $Y^3$ and $Y^4$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$ may be bonded with each other to form a cycloalkyl group or an aryl group.

Examples of the compound of the formula 1 include the following compound represented by formula 1-2.

Formula 1-2

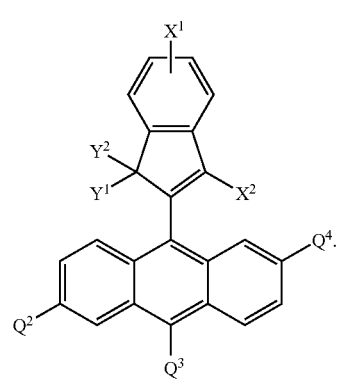

wherein $Q^2$ to $Q^4$, $X^1$, $X^2$, $Y^1$ and $Y^2$ are as defined in Formula (1).

Examples of the compound of the formula 1 include the following compound represented by formula 1-3.

Formula 1-3

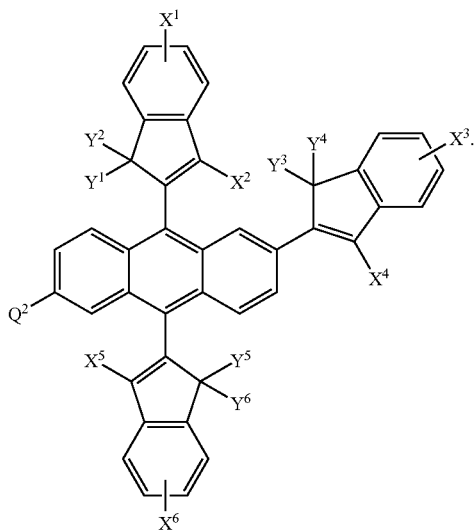

wherein $Q^2$, $X^1$, $X^2$, $Y^1$ and $Y^2$ are as defined in Formula (1), $X^3$ to $X^6$ and $Y^3$ to $Y^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$ or $Y^5$ and $Y^6$ may be bonded with each other to form a cycloalkyl group or an aryl group.

Examples of the compound of the formula 1 include the following compound represented by formula 1-4.

Formula 1-4

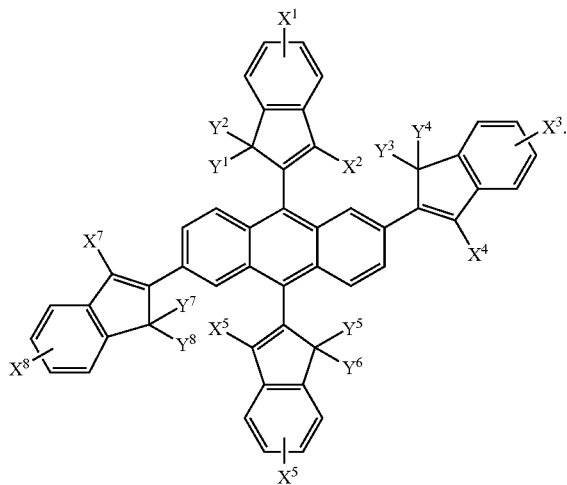

wherein $X_1$, $X^2$, $Y^1$ and $Y^2$ are as defined in Formula (1), $X^3$ to $X^8$ and $Y^3$ to $Y^8$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$. $Y^5$ and $Y^6$ or $Y^7$ and $Y^8$ may be bonded with each other to form a cycloalkyl group or an aryl group.

Examples of the compound of the formula 1 include the following compound represented by formula 1-5.

Formula 1-5

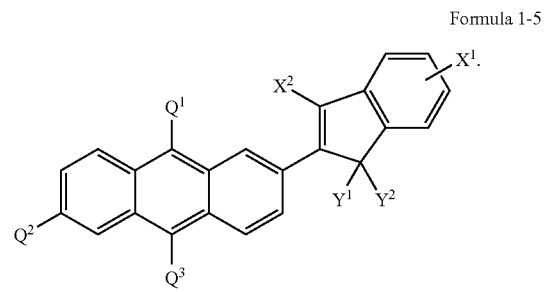

wherein $Q^1$ to $Q^3$, $X^1$, $X^2$, $Y^1$ and $Y^2$ are as defined in Formula (1).

The following illustrates specific examples of the compound of the formula (1), but the scope of the invention is not limited only thereto.

(1-1-1)

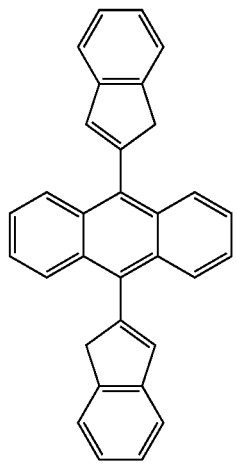

-continued
(1-1-2)
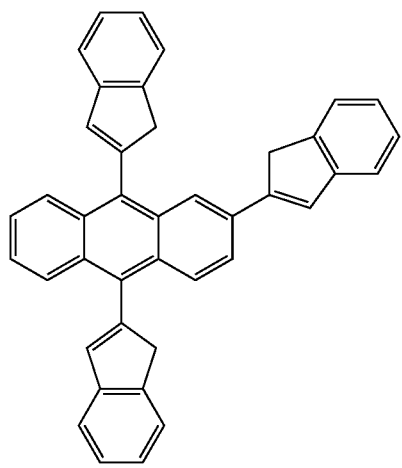
(1-1-3)
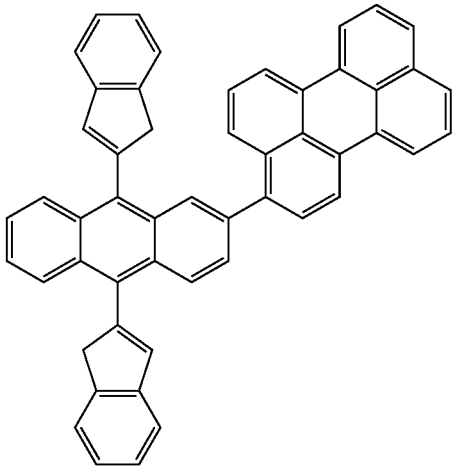
(1-1-4)
(1-1-5)
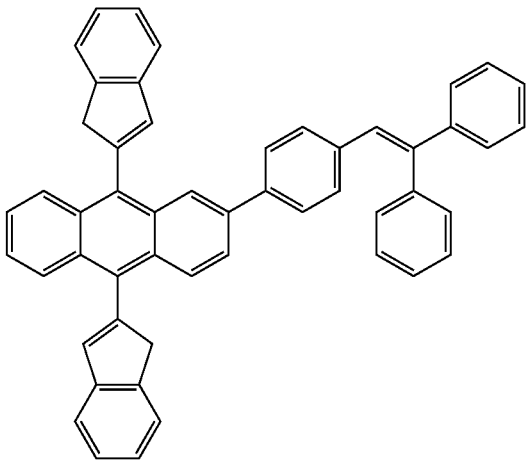
(1-1-6)
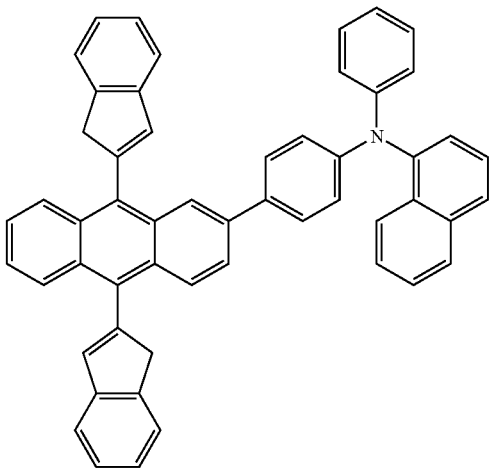
(1-1-7)

-continued
(1-1-8)
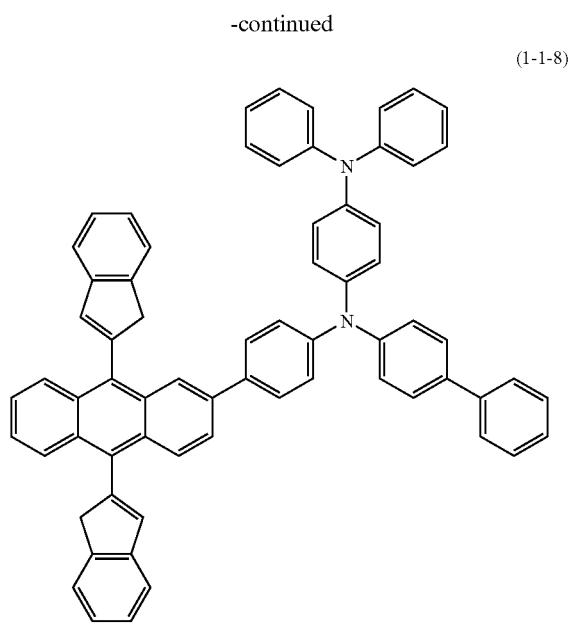
(1-1-9)
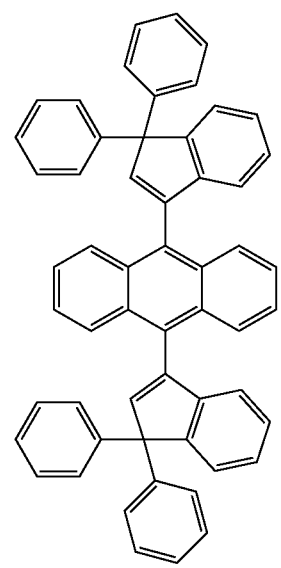
(1-1-10)
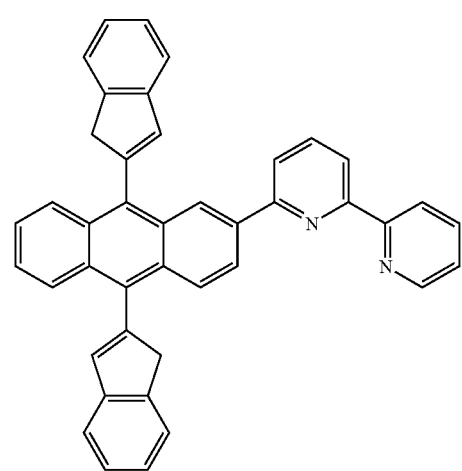
-continued
(1-1-11)
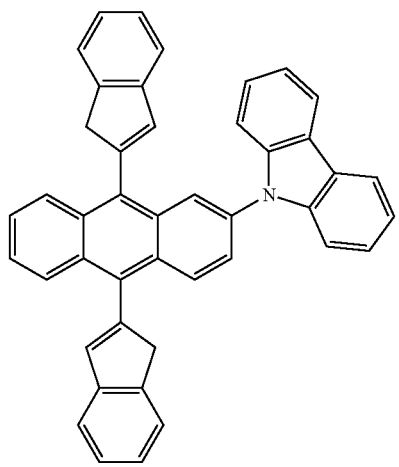
(1-1-12)
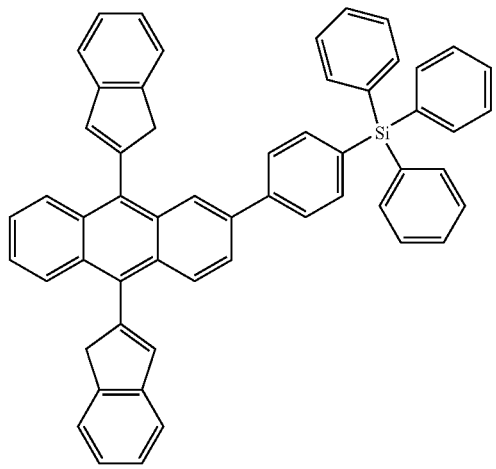
(1-1-13)
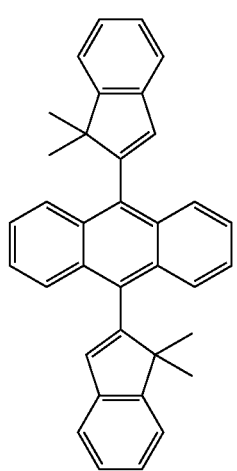

-continued
(1-1-14)
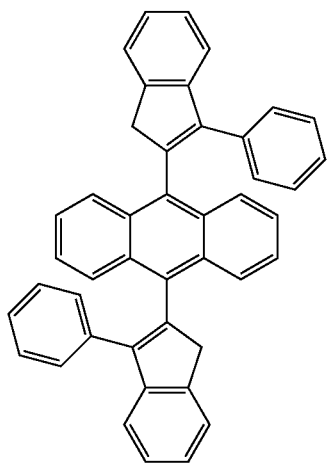
(1-1-15)
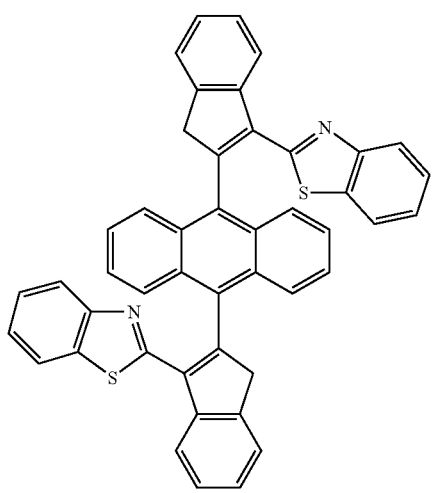
(1-1-16)
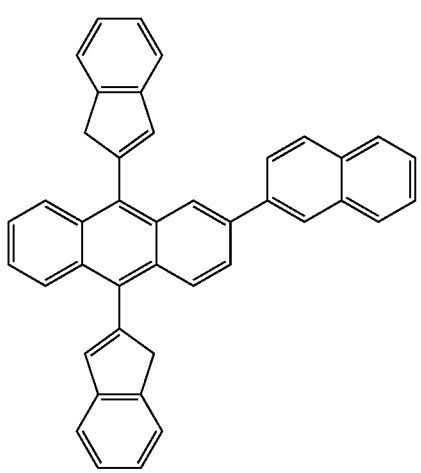
-continued
(1-1-17)
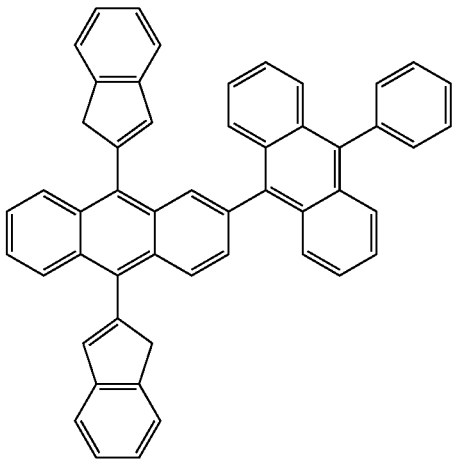
(1-1-18)
(1-2-1)
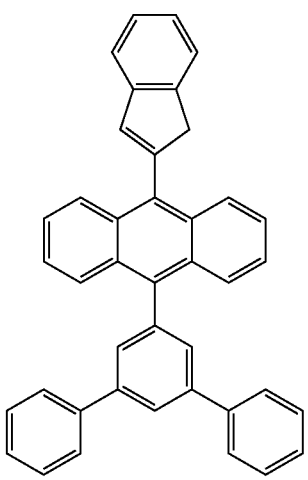

-continued
(1-2-2)
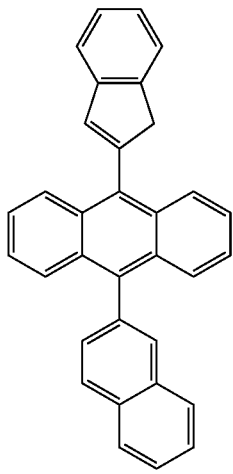
(1-2-3)
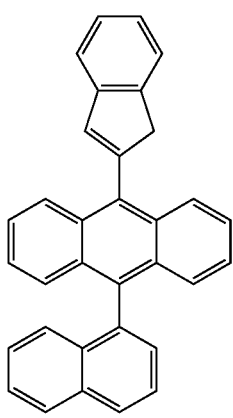
(1-2-4)
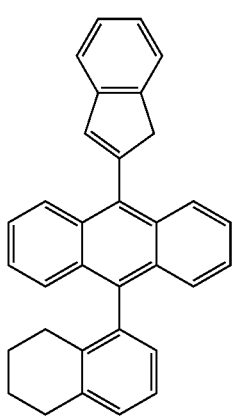
-continued
(1-2-5)
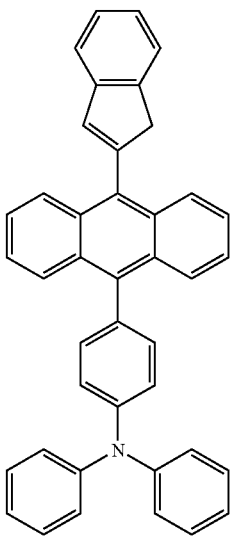
(1-2-6)
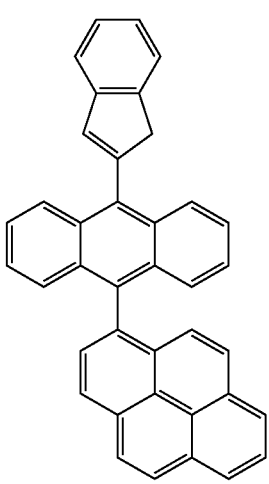
(1-3-1)
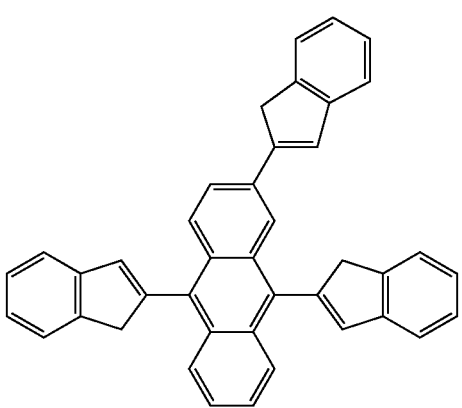

-continued
(1-3-2)
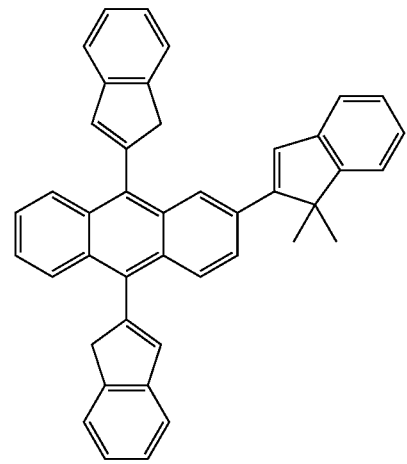
(1-4-1)
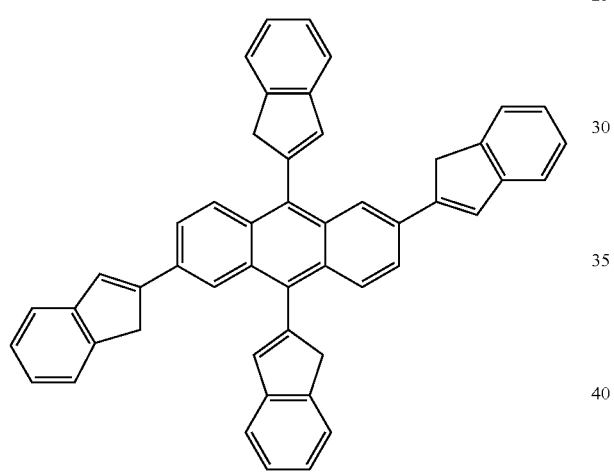
(1-4-2)
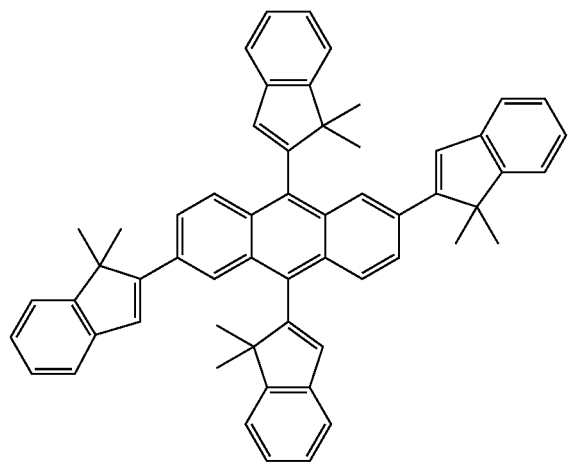
-continued
(1-5-1)
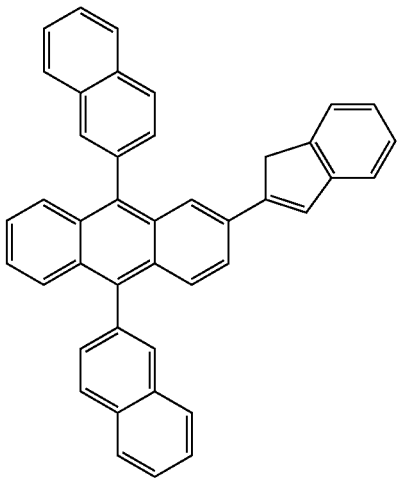
(1-5-2)
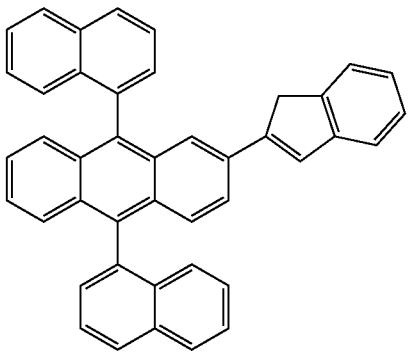
(1-5-3)
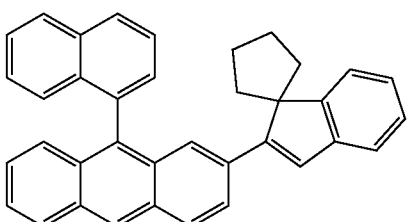
(1-5-4)
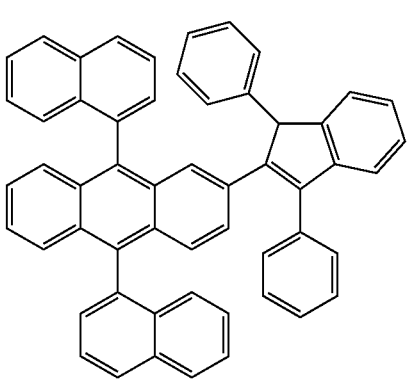

-continued (1-5-5)

(1-5-6)

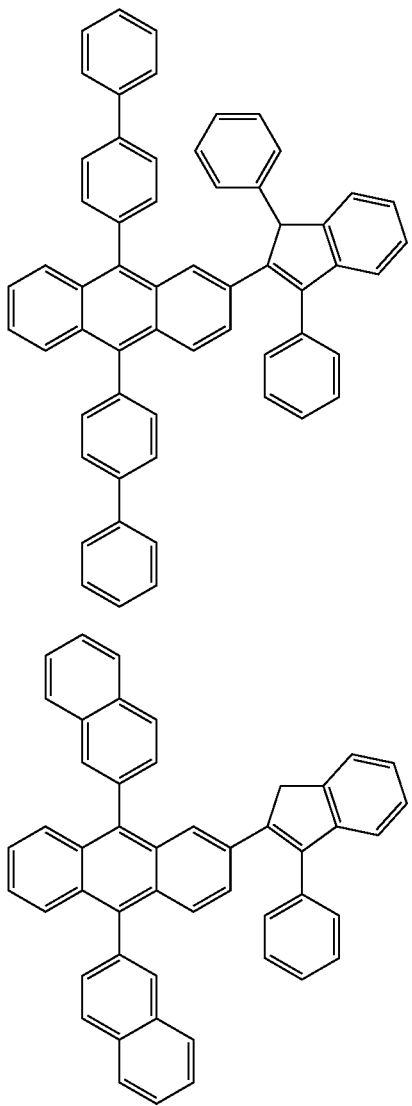

The compounds of the formula 1 can be prepared by introducing an indene group to anthracene. More particularly, the compounds of the formula 1 can be prepared by reacting indenyl-2-boronic acid and anthracene halide compound applying a Susuki-bonding reaction so as to introduce an indene group to anthracene. The substituents except the indene group in the compound of the formula 1 may be substituted using known methods such as a Susuki-bonding reaction, other condensation reaction or dehydration reaction. In one embodiment according to the present invention, the compound of the formula 1 can be prepared by a method comprising the steps of a) introducing a hydroxy group and a bromo group to substituted or unsubstituted indene, using N-bromosuccinimide; b) introducing a boron compound to the compound obtained from the step a), using metal such as magnesium: c) introducing the compound obtained from the step b) to a substituted or unsubstituted anthracene, using transition metal such as palladium.

The compound according to the present invention can be applied to an organic light-emitting diode by the general production method of the organic light-emitting diode in one embodiment of the invention, the organic light-emitting diode has a structure comprising a first electrode, a second electrode and an organic material layer arranged therebetween, and can be produced by the general production method and materials of the organic electronic diode, except that the compound according to the invention is used in an organic material layer of the organic light-emitting diode. The compound according to the present invention serves as a hole-injection, hole-transport, light-emitting or electron-transport material, more preferably a light-emitting material in the organic light-emitting diode.

For example, the organic light-emitting diode according to the invention can be produced by depositing metals or metal oxides having electrical conductivity, or metal alloys thereof on a substrate to form an anode, forming thereon an organic material layer comprising a hole-injecting layer, a hole-transporting layer, a light-emitting layer and an electron-transporting layer and then depositing on the organic material layer a material capable of using as a cathode, using a PVD (physical vapor deposition) technique such as sputtering and e-beam evaporation.

In addition to this method, the organic light-emitting diode can be also fabricated by sequentially depositing a cathode material, an organic material layer and an anode material, on the substrate (see International Publication No. WO 03/012890). The organic material layer may be of a multilayer structure comprising the hole-injecting layer, the hole-transporting layer, the light-emitting layer, the electron-transporting layer and the like, but not limited thereto, and may be of a monolayer structure. Further, the organic material layer can be produced in a smaller number of layers with various polymer materials by using not a vacuum deposition method but a solvent process such as spin coating, dip coating, doctor blade coating, screen printing, inkjet printing, heat transfer method or the like.

The anode materials are preferably materials having large work function for facilitating usually hole injection into the organic material layer. Specific examples of the anode materials usable in the invention include metals such as vanadium, chrome, copper, zinc and gold or alloys thereof; metal oxides such as zinc oxide, indium oxide, indium tin oxide (ITO) and indium zinc oxide (IZO): metal/oxide composites such as $ZnO:Al$ or $SnO_2:Sb$; and conductive polymers such as poly(3-methylthiophene), poly[3,4-(ethylene-1,2-dioxy)thiophene] (PEDT), polypyrrole and polyaniline, but are not limited thereto.

The cathode materials are preferably materials having small work function for facilitating usually electron injection into the organic material layer. Specific examples of the cathode materials include metals such as magnesium, calcium, sodium, potassium, titanium, indium, yttrium, lithium, gadolinium, aluminum, silver, tin and lead or alloys thereof; and multilayered materials such as LiF/Al or $LiO_2/Al$, but are not limited thereto.

The hole-injecting material is a material facilitating hole injection from an anode at low voltage. The HOMO (highest occupied molecular orbital) level of the hole-injecting material is preferably located between the work function of the anode materials and the HOMO level of its neighboring organic material layer. Specific examples of the hole-injecting material include metal porphyrin, oligothiophene, arylamine-based organic materials, hexanitrile hexaazatriphenylene, quinacridone based organic materials, perylene-based organic materials, antraquinone, and polyaniline-based and polythiophene-based conductive polymers, but are not limited thereto.

The hole-transporting material is suitably a material having high hole mobility, which can transfer holes from the anode or the hole-injecting layer toward the light-emitting layer. Specific examples thereof include arylamine-based organic materials, conductive polymers and block copolymers having both conjugated portions and non-conjugated portions, but are not limited thereto.

The light-emitting material are a material capable of emitting visible light by accepting and recombining holes from the hole-transporting layer and electrons from the electron-transporting layer, preferably a material having high quantum efficiency for fluorescence and phosphorescence. Specific examples thereof include 8-hydroxyquinoline aluminum complex (Alq$_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene)(PPV)-based polymers; spiro compounds; and polyfluorene and rubrene, but are not limited thereto.

The electron-transporting material is suitably a material having high electron mobility, which can transfer electrons from the cathode to the light-emitting layer. Specific examples thereof include 8-hydroxyquinoline aluminum complex (Alq$_3$); complexes including Alq$_3$; organic radical compounds; and hydroxyflavone-metal complexes, but are not limited thereto.

The organic light-emitting diode according to the invention may be of a top emission structure, a bottom emission structure or a top and bottom emission structure according to the materials used.

MODE FOR INVENTION

Hereinafter, the present invention will be described in more detail by means of Synthesis Examples and Experimental Examples, but the scope of the invention is not limited thereto.

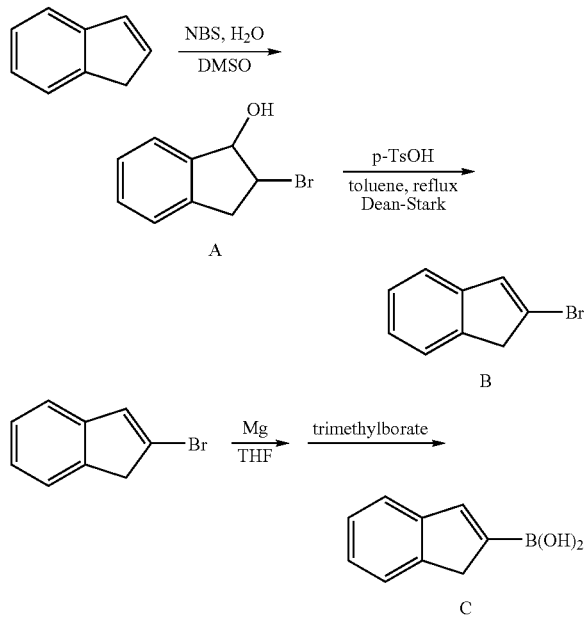

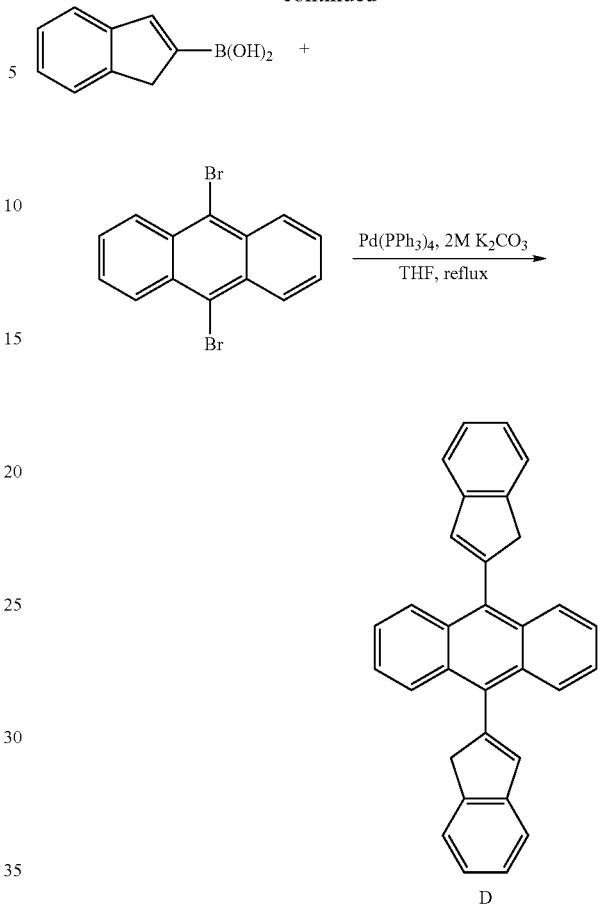

Synthesis of Compound A

To dimethylsulfoxide (DMSO, 90 ml), indene (258 mmol, 30 g) and distilled water (9 ml) were added and cooled to 0° C. N-bromosuccinimide (NBS, 263 mmol, 46.9 g) was added thereto slowly. The obtained mixture was heated to normal temperature and stirred for 12 hours. After the mixture was cooled to 0° C., the reaction was completed by using distilled water. An organic layer was extracted with diethylether and dried over anhydrous magnesium sulfate, It was filtered under reduced pressure and the filtered solution was dried under reduced pressure and recrystalized with hexane to obtain the compound A(38.9 g, 72%).

$^1$H NMR (300 MHz, CDCl$_3$):δ 2.80 (s, 1H), 3.20 (dd, 1H), 4.20 (m, 1H), 7.19-7.37 (m, 4H)

Synthesis of Compound B

The compound A (67 mmol, 14.3 g) and p-toluenesulfonic acid (p-TsOH, 2.6 mmol, 0.5 g) were dissolved in toluene (60 ml). The solution was heated and stirred for 24 hours while water was removed using a Dean-Stark method. The mixture was cooled to normal temperature, dried under reduced pressure and subjected to fractional distillation to obtain the Compound B (7.8 g, 60%).

$^1$H NMR (300 MHz, CDCl$_3$):δ 3.72 (m, 2H), 7.00 (m, 1H), 7.25-7.52 (m, 4H)

Synthesis of Compound C

To purified tetrahydrofuran (THF, 200 ml), magnesium (51.3 mmol) and 1,2-dibromoethane (cat amount) were added and cooled to 0° C. 2-bromoindene was slowly added thereto. The reaction solution was heated to normal temperature and stirred for 2 hours. The reaction solution was cooled to −78° C. and trimethyl borate (51.3 mmol, 5.72 ml) was added slowly thereto. Then, the solution was slowly heated to normal temperature and stirred for 8 hours. Then, 1N solution of hydrochloric acid was added. The solution was stirred for one hour and extracted with diethylether. The obtained organic layer was washed with brine. The obtained material was dried over anhydrous magnesium sulfate (Na$_2$SO$_4$) and filtered under reduced pressure. The filtered solution was dried under redued pressure and recrystalized with diethyl ether/n-hexane to obtain the compound C (2.9 g, 58%).

$^1$H NMR (300 MHz, CDCl$_3$):δ 2.30 (s, 2H), 3.84 (m, 2H), 7.20 (m, 1H), 7.20-7.39 (m, 4H)

Synthesis of the Compound of Formula 1-1-1 (Compound D)

To purified tetrahydrofuran (THF, 25 ml), 9,10-dibromoanthracene (2.53 mmol, 0.85 g) and the compound C (5.05 mmol, 658 mg) were added and dissolved entirely by being heated and stirred. Then, tetrabistriphenylphosphinopalladium (Pd(PPh$_3$)$_4$, 0.05 mmol, 58 mg) and 2M potassium, carbonate (2 M K$_2$CO$_3$, 25 ml) were added thereto, and heated and stirred for 12 hours. After the reaction solution was cooled to normal temperature, the produced precipitation was filtered under reduced pressure to obtain the compound D [Formula 1-1-1 (600 mg, 60%)]

MS: [M+H]$^+$=407

Synthesis Example 2

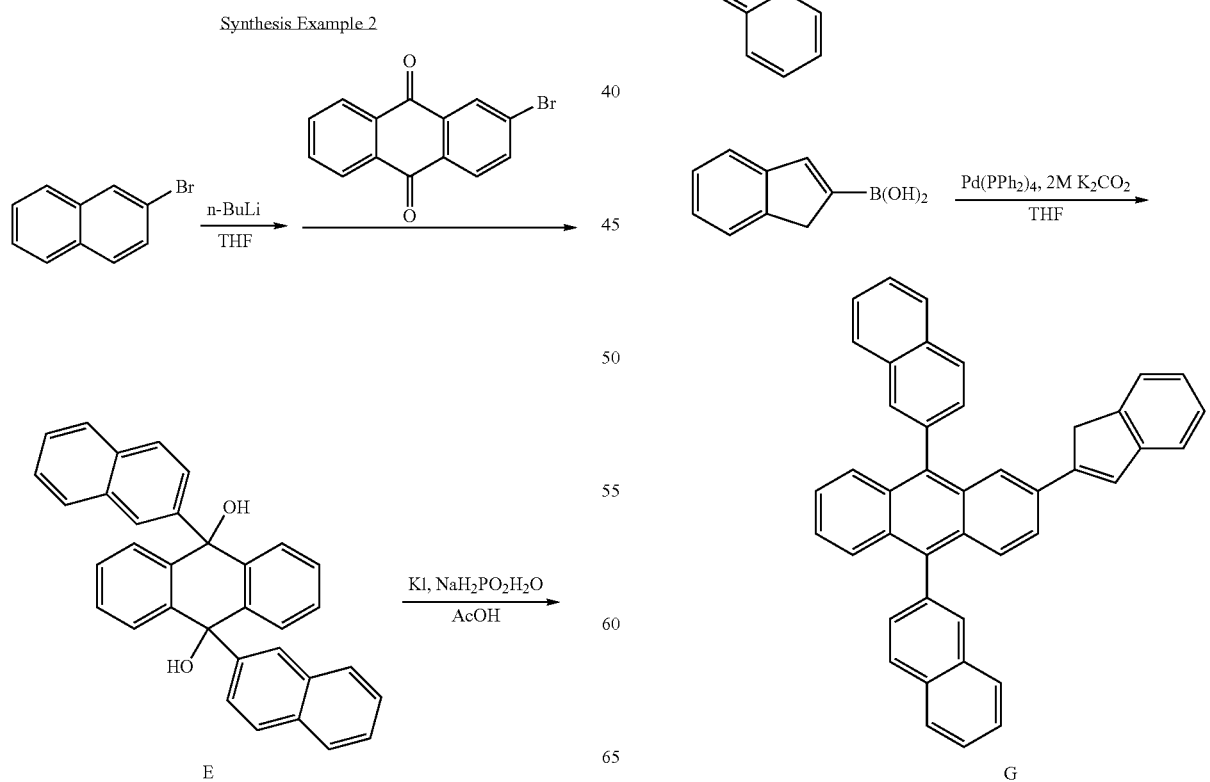

Synthesis of Compound E 2-bromonaphthalene (34.8 g, 168 mmol) was dissolved in THF (170 ml). The solution was cooled to −78° C. and 2.5M of n-BuLi (67.3 mL, 168 mmol) was slowly added thereto and stirred for one hour. Then, 2-bromoanthraquinone (21 g, 73.1 mmol) was added and the reaction solution was stirred for 2 hours while it was slowly heated to normal temperature. Aqueous solution of ammonium chloride was added. An organic layer was separated, dried over magnesium sulfate and filtered. The filtered solution was dried under reduced pressure to remove solvents and recrystalized with diethyl ether to obtain the compound E (32.3 g, 82%).

MS: $[M+H]^+$=465

Synthesis of Compound F

To acetic acid (150 mL), the compound E(32.3 g, 59.5 mmol), a potassium iodide (29.6 g, 178.4 mmol) and a hypophosphite soda (38.0 g, 356.8 mmol) were added and then heated and stirred for 6 hours. The solution was cooled to normal temperature, and then the produced precipitation was filtered, washed with water and dried to obtain the compound F (25.5 g, 84%).

MS: $[M+H]^+$=510

Synthesis of Compound G

The compound F(2.0 g, 3.9 mmol) and indenyl boronic acid (520 mg, 4.0 mmol) were entirely dissolved in tetrahydrofuran (50 mL). Then 2 M aqueous solution of potassium carbonate (50 mL) was added and palladium catalyst (23 mg, $1.9 \times 10^{-2}$ mmol) was added. The reaction solution was heated and stirred to obtain the compound G (Formula 1-5-1, 1.2 g, 57%).

MS: $[M+H]^+$=545

EXPERIMENTAL EXAMPLE 1

A glass substrate on which a thin film of ITO (indium tin oxide) was coated to a thickness of 1500 Å was immersed in distilled water containing a detergent to wash the substrate with ultrasonic waves for 30 minutes (At this time, the detergent was a product commercially available from Fisher Co. and the distilled water has been filtered twice by using a filter commercially available from Millipore Co.). Next, washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried and transferred to a plasma cleaner. Then, the substrate was cleaned for 5 minutes by using oxygen plasma and transferred to a vacuum deposition device.

On the ITO transparent electrode thus prepared hexanitrile hexaazatriphenylene (HAT) represented by following formula was coated to a thickness of 500 Å by thermal vacuum deposition, thereby forming a hole-injecting layer.

[HAT]

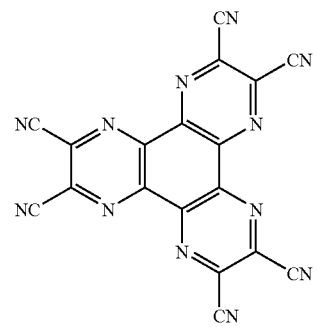

On the hole-injecting layer, NPB represented by following formula as a hole-transporting material was coated to a thickness of 400 Å by vacuum deposition, thereby forming a hole-transporting layer.

[NPB]

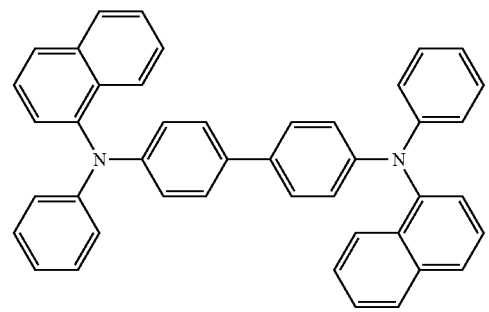

Then, on the hole-transporting layer, the compound of formula 1-1-1 synthesized in Synthesis Example 1, as a light-emitting host, was coated to a thickness of 300 Å by vacuum deposition to form a light-emitting layer. On the light-emitting layer, an Alq3 (aluminum tris(8-hydroxyquinoline)) represented by following formula was coated to a thickness of 200 Å by vacuum deposition to form an electron-injecting/transporting layer.

[Alq3]

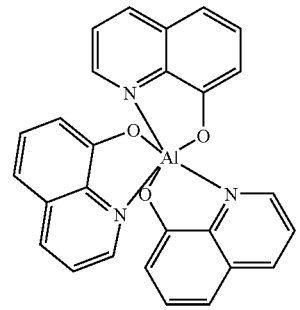

Next, on the electron-injecting/transporting layer, lithium fluoride (LiF) and aluminum were sequentially vacuum-deposited to a thickness of 12 Å and 2000 Å, respectively, to form a cathode.

In the above process, deposition rate of each organic material was maintained at 0.4 to 0.7 Å/sec and deposition rates of lithium fluoride and aluminum were maintained at 0.3 Å/sec and 2 Å/sec, respectively. The vacuum degree during deposition was maintained at $2\times10^{-7}$ to $5\times10^{-8}$ torr.

When a forward electric field of 5.8 V was applied to the organic light-emitting diode prepared above, blue light emission was observed with x=0.16 and y=0.18 based on the 1931 CIE color coordinate at a current density of 50 mA/cm², When a forward electric field of 6.7 V was applied, blue light emission of 2.1 cd/A was observed at a current density of 100 mA/cm².

EXPERIMENTAL EXAMPLE 2

A glass substrate (Corning 7059 glass) on which a thin film of ITO (indium tin oxide) was coated to a thickness of 1000 Å was immersed in distilled water containing a detergent to wash the substrate with ultrasonic waves for 30 minutes (At this time, the detergent was a product commercially available from Fisher Co. and the distilled water has been filtered previously by using a filter commercially available from Millipore Co.). Next, washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried.

On the ITO electrode thus prepared, hexanitrile hexaazatriphenylene, 4,4'-bis [N-(1-naphthyl)-N-phenylamino]biphenyl (NPB), the compound of the formula 1-1-1 and Alq3 were sequentially coated to thicknesses of 500 Å, 400 Å, 300 Å and 200 Å by thermal vacuum deposition, thereby forming a hole-injecting layer, a hole-transporting layer, a light-emitting layer and an electron-transporting layer in this order.

On the electron-transporting layer, lithium fluoride (LiF) and aluminum were sequentially vacuum-deposited to a thickness of 12 Å and 2000 Å, respectively, to form a cathode. Thus, an organic light-emitting device was produced.

In the above process, deposition rate of each organic material was maintained at 0.4 to 0.7 Å/sec and deposition rates of lithium fluoride and aluminum of the cathode were maintained at 0.3 Å/sec and 2 Å/sec, respectively. The vacuum degree during deposition was maintained at $2\times10^{-7}$ to $5\times10^{-8}$ torr.

When a forward electric field of 6.4 V was applied to the organic light-emitting device prepared above, blue light emission was observed with x=0.16 and y=0.21 based on the 1931 CIE color coordinate at a current density of 50 mA/cm². When a forward electric field of 7.2 V was applied, blue light emission of 1.8 cd/A was observed at a current density of 100 mA/cm².

EXPERIMENTAL EXAMPLE 3

A glass substrate (Corning 7059 glass) on which a thin film of ITO (indium tin oxide) was coated to a thickness of 1000 Å was immersed in distilled water containing a detergent to wash the substrate with ultrasonic waves for 30 minutes (At this time, the detergent was a product commercially available from Fisher Co. and the distilled water has been filtered previously by using a filter commercially available from Millipore Co.). Next, washing with ultrasonic waves was repeated twice for 10 minutes by using distilled water. After the completion of washing with distilled water, washing with ultrasonic waves was carried out by using solvents such as isopropyl alcohol, acetone and methanol. The resultant product was dried.

On the ITO electrode thus prepared, hexanitrile hexaazatriphenylene, 4,4'-bis (N-(1-naphthyl)-N-phenylamino 3 biphenyl (NPB), the compound of the formula 1-5-1 and Alq3 were sequentially coated to thicknesses of 500 Å, 400 Å, 300 Å and 200 Å by thermal vacuum deposition, thereby forming a hole-injecting layer, a hole-transporting layer, a light-emitting layer and an electron-transporting layer in this order.

On the electron-transporting layer, lithium fluoride (LiF) and aluminum were sequentially vacuum-deposited to a thickness of 12 Å and 2000 Å, respectively, to form a cathode. Thus, an organic light-emitting device was produced.

In the above process, deposition rate of each organic material was maintained at 0.4 to 0.7 Å/sec and deposition rates of lithium fluoride and aluminum of the cathode were maintained at 0.3 Å/sec and 2 Å/sec, respectively. The vacuum degree during deposition was maintained at $2\times10^{-7}$ to $5\times10^{-8}$ torr.

When a forward electric field of 6.4 V was applied to the organic light-emitting device prepared above, blue light emission was observed with x=0.21 and y=0.24 based on the 1931 CIE color coordinate at a current density of 50 mA/cm². When a forward electric field of 7.3 V was applied, blue light emission of 3.0 cd/A was observed at a current density of 100 mA/cm².

What is claimed is:

1. An indene derivative represented by the following formula (1):

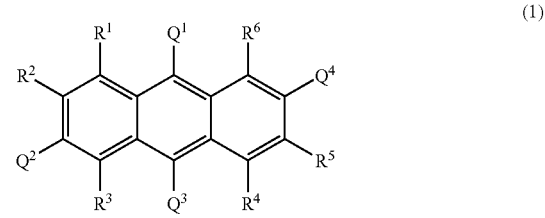

(1)

wherein at least one of $Q^1$ to $Q^4$ to are a group represented by the following formula (2), the reminders of $Q^1$ to $Q^4$ that are not represented by the following formula (2) and $R^1$ to $R^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted cycloalkyl group, a substituted or unsubstituted cycloalkenyl group, a substituted or unsubstituted aryl group, a substituted or unsubstituted arylamine group, a substituted or unsubstituted heterocyclic group, a substituted or unsubstituted silane group, a substituted or unsubstituted boric group, a substituted or unsubstituted amino group, a nitrile group, a nitro group, a halogen group, a substituted or unsubstituted amide group, and a substituted or unsubstituted ester group, and they may be bonded with an adjacent group to form an aliphatic, aromatic or hetero fused ring,

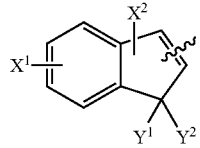

(2)

wherein $X^1$, $X^2$, $Y^1$ and $Y^2$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^1$ and $Y^2$ may be bonded with each other to form a cycloalkyl group or an aryl group.

2. The indene derivative according to claim 1, wherein the compound of the formula (1) is selected from the group consisting of the compounds of the following formulae (1-1) to (1-5):

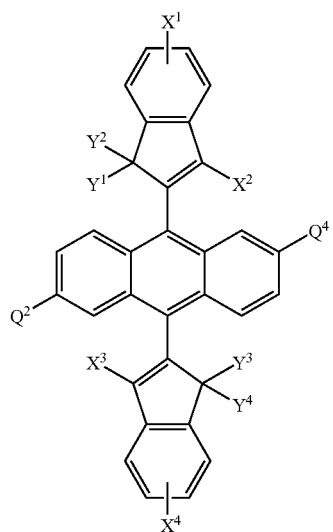

(1-1)

wherein $Q^2$, $Q^4$, $X^2$, $X^2$, $Y^1$ and $Y^2$ are as defined in Formula (1),
$X^3$, $X^4$, $Y^3$ and $Y^4$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$ may be bonded with each other to form a cycloalkyl group or an aryl group,

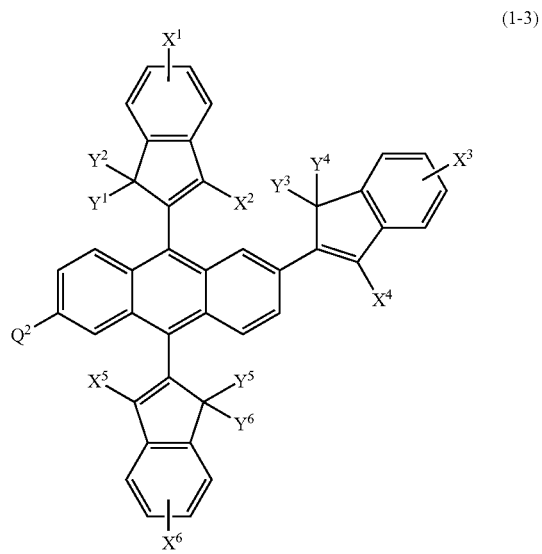

(1-2)

wherein $Q^2$ to $Q^4$, $X^1$, $X^2$, $Y^1$ and $Y^2$ are as defined in Formula (1), (1-3)

wherein $Q^2$, $X^1$, $X^2$, $Y^1$ and $Y^2$ are as defined in Formula (1),
$X^3$ to $X^6$ and $Y^3$ to $Y^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$ or $Y^5$ and $Y^6$ may be bonded with each other to form a cycloalkyl group or an aryl group,

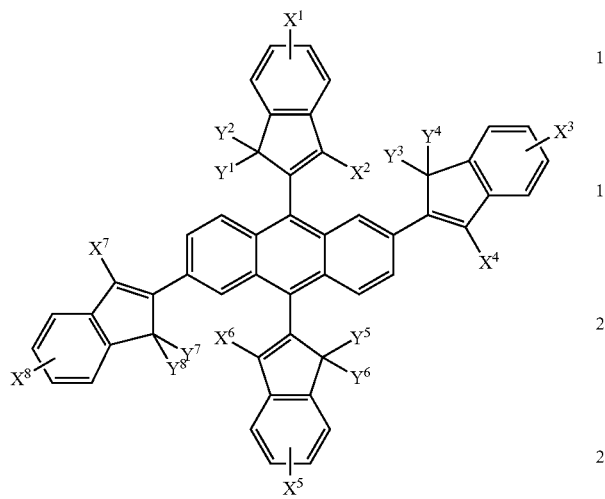

(1-4)

wherein $X^1$, $X^2$, $Y^1$ and $Y^2$ are as defined in Formula (1), $X^3$ to $X^8$ and $Y^3$ to $Y^8$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^3$ and $Y^4$, $Y^5$ and $Y^6$ or $Y^7$ and $Y^8$ may be bonded with each other to form a cycloalkyl group or an aryl group,

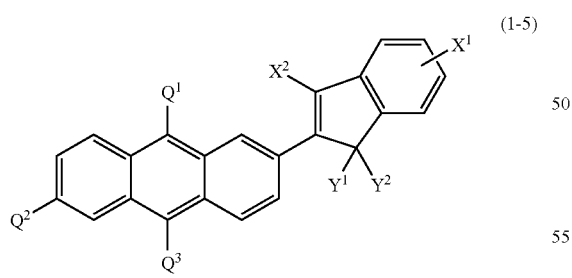

(1-5)

wherein $Q^1$ to $Q^3$, $X^1$, $X^2$, $Y^1$ and $Y^2$ are as defined in Formula (1).

3. A method for preparing the compound of the following formula (1), comprising the steps of a) introducing a hydroxy group and a bromo group to substituted or unsubstituted indene, using N-bromosuccinimide; b) introducing a boron compound to the compound obtained from the step a), using a metal; and c) introducing the compound obtained from the step b) to substituted or unsubstituted anthracene, using a transition metal:

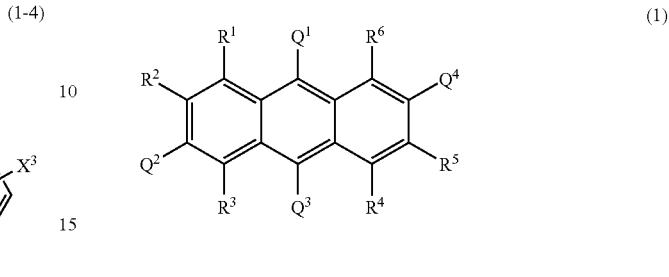

(1)

wherein at least one of $Q^1$ to $Q^4$ are a group represented by the following formula (2), the reminders of $Q^1$ to $Q^4$ that are not represented by the following formula (2) and $R^1$ to $R^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted cycloalkyl group, a substituted or unsubstituted cycloalkenyl group, a substituted or unsubstituted aryl group, a substituted or unsubstituted arylamine group, a substituted or unsubstituted heterocyclic group, a substituted or unsubstituted silane group, a substituted or unsubstituted boric group, a substituted or unsubstituted amino group, a nitrile group, a nitro group, a halogen group, a substituted or unsubstituted amide group, and a substituted or unsubstituted ester group, and they may be bonded with an adjacent group to form an aliphatic, aromatic or hetero fused ring,

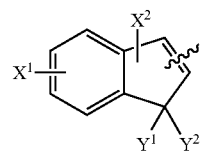

(2)

wherein $X^1$, $X^2$ $Y^1$ and $Y^2$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^1$ and $Y^2$ may be bonded with each other to form a cycloalkyl group or an aryl group.

4. An organic light-emitting diode comprising a first electrode, a second electrode and an organic material layer arranged between the first electrode and the second electrode, in which the organic material layer comprises the compound of formula (1):

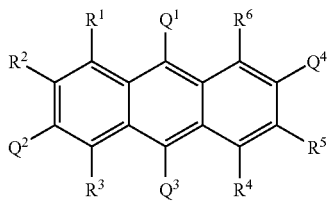

(1)

wherein at least one of $Q^1$ to $Q^4$ are a group represented by the following formula (2), the reminders of $Q^1$ to $Q^4$ that are not represented by the following formula (2) and $R^1$ to $R^6$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted cycloalkyl group, a substituted or unsubstituted cycloalkenyl group, a substituted or unsubstituted aryl group, a substituted or unsubstituted arylamine group, a substituted or unsubstituted heterocyclic group, a substituted or unsubstituted silane group, a substituted or unsubstituted boric group, a substituted or unsubstituted amino group, a nitrile group, a nitro group, a halogen group, a substituted or unsubstituted amide group, and a substituted or unsubstituted ester group, and they may be bonded with an adjacent group to form an aliphatic, aromatic or hetero fused ring,

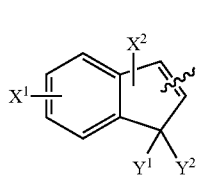

(2)

wherein $X^1$, $X^2$ $Y^1$ and $Y^2$ are respectively or simultaneously selected from the group consisting of a hydrogen, a substituted or unsubstituted straight or branched alkyl group, a substituted or unsubstituted straight or branched alkoxy group, a substituted or unsubstituted straight or branched alkenyl group, a substituted or unsubstituted heterocyclic group, a substituted or unsubstituted cycloalkyl group, a substituted or unsubstituted aryl group, and a substituted or unsubstituted arylamine group, and $Y^1$ and $Y^2$ may be bonded with each other to form a cycloalkyl group or an aryl group.

5. The organic light-emitting diode according to claim 4, wherein the organic material layer comprises a light-emitting layer and the light-emitting layer comprises the compound of formula (1).

6. The organic light-emitting diode according to claim 5, wherein the organic material layer additionally comprises at least one layer selected from the group consisting of a hole-injecting layer, a hole-transporting layer, an electron-injecting layer and an electron-transporting layer.

* * * * *